United States Patent
Elbe et al.

(10) Patent No.: US 6,369,093 B1
(45) Date of Patent: Apr. 9, 2002

(54) PYRAZOLE CARBOXANILIDE FUNGICIDE

(75) Inventors: Hans-Ludwig Elbe, Wuppertal; Astrid Mauler-Machnik, Leichlingen; Klaus Stenzel, Düsseldorf; Karl-Heinz Kuck, Langenfeld; Martin Kugler, Leichlingen; Thomas Jaetsch, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/786,211

(22) PCT Filed: Aug. 23, 1999

(86) PCT No.: PCT/EP99/06149

§ 371 Date: Mar. 1, 2001

§ 102(e) Date: Mar. 1, 2001

(87) PCT Pub. No.: WO00/14071

PCT Pub. Date: Mar. 16, 2000

(30) Foreign Application Priority Data

Sep. 4, 1998 (DE) .......................... 198 40 322

(51) Int. Cl.⁷ ..................... A01N 31/56; C07D 231/14
(52) U.S. Cl. ..................... 514/406; 548/374.1
(58) Field of Search ................. 548/374.1; 514/406

(56) References Cited

U.S. PATENT DOCUMENTS

| 5,480,897 A | 1/1996 | Eicken et al. |
| 5,556,988 A | 9/1996 | Eicken et al. |
| 5,589,493 A | 12/1996 | Eicken et al. |
| 6,147,104 A | 11/2000 | Eicken et al. ............ 514/406 |

FOREIGN PATENT DOCUMENTS

| EP | 0 589 301 | 3/1994 |
| EP | 0 776 889 | 6/1997 |
| WO | 97/08148 | 3/1993 |
| WO | 93/11117 | 6/1993 |
| WO | 98/03500 | 1/1998 |
| WO | 99/09013 | 2/1999 |

OTHER PUBLICATIONS

Database Chemabs, Chemical Abstracts Service, Columbus, Ohio, Yoshikawa, Yukihiro et al: "Preparation of pyrazole-carboxyanilide derivatives as agrochemical fungicides" retrieved from STN Database accession No. 127:5086 XP002135650, & JP 09 132567 A (Mistsui Toatsu Chemicals, Inc., Japan, May 20, 1997.

Primary Examiner—Robert W. Ramsuer
(74) Attorney, Agent, or Firm—Joseph C. Gil

(57) ABSTRACT

Novel pyrazole-carboxanilides of the formula

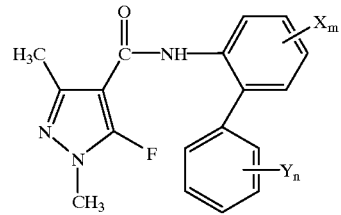

(I)

in which
X, Y, m and n are each as defined in the description,
a process for preparing these substances and their use for controlling undesirable microorganisms.

14 Claims, No Drawings

PYRAZOLE CARBOXANILIDE FUNGICIDE

This application is a 371 of PCT/EP99/06149 filed Aug. 23, 1999.

FIELD OF THE INVENTION

The present invention relates to novel pyrazole-carboxanilides, to a process for their preparation and to their use for controlling undesirable microorganisms.

BACKGROUND OF THE INVENTION

It is already known that numerous carboxanilides have fungicidal properties (compare WO 93/11 117, EP-A 0 545 099 and EP-A 0 589 301). Thus, N-(2-cyclohexyl)-1,3-dimethyl-5-fluoropyrazole-4-carboxanilide, N-(2-phenyl)-1,3-dimethyl-pyrazole-4-carboxanilide and N-[2-(2-fluorophenyl)]-1,3-dimethyl-pyrazole-4-carboxanilide can be used for controlling fungi. The activity of these substances is good, however, it is sometimes unsatisfactory at low application rates.

SUMMARY OF THE INVENTION

Pyrazole-carboxanilides of the formula

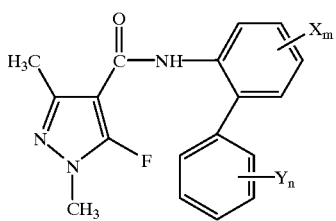

(I)

wherein m, n, X and Y are as described may be used for controlling undesirable microorganisms.

DETAILED DESCRIPTION

This invention, accordingly, provides novel pyrazole-carboxanilides of the formula

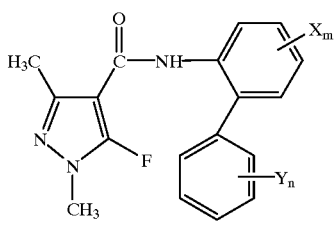

(I)

in which
a) m represents the number 0,
 n represents the number 1 and
 Y represents 2-chloro, 2-fluoro, 4-bromo, 2-methyl, 2-trifluoromethyl, 3-trifluoromethyl,
  represents nitro, cyano, hydroxyl, carboxyl, halogenoalkoxy having 1 to 6 carbon atoms and 1 to 5 halogen atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety,
 or
b) m represents the number 0,
 n represents the number 2 or 3 and
 Y represents halogen, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety,
 or
c) m represents the number 1,
 X represents chlorine, bromine, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety,
 n represents integers from 0 to 3 and
 Y represents halogen, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety.

Furthermore, it has been found that pyrazole-carboxanilides of the formula (I) are obtained by reacting acyl halides of the formula

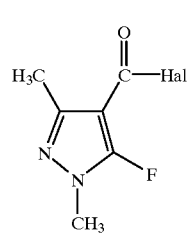

(II)

in which
Hal represents halogen with aniline derivatives of the formula

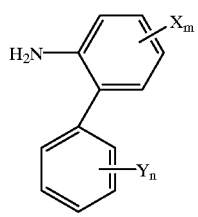

(III)

in which

X, Y, m and n are each as defined above,
if appropriate in the presence of an acid binder and if appropriate in the presence of a diluent.

Finally, it has been found that the novel pyrazole-carboxanilides of the formula (I) have very good microbicidal properties and can be used for controlling undesirable microorganisms, both in crop protection and in the protection of materials.

Surprisingly, the pyrazole-carboxanilides of the formula (I) according to the invention have considerably better fungicidal activity than N-(2-cyclohexyl)-1,3-dimethyl-5-fluoropyrazole-4-carboxanilide, N-(2-phenyl)-1,3-dimethyl-pyrazole-4-carboxanilide and N-[2-(2-fluoro-phenyl)]-1,3-dimethyl-pyrazole-4-carboxanilide, which are the constitutionally most similar active compounds of the prior art of the same direction of action.

The formula (I) provides a general definition of the pyrazole-carboxanilides according to the invention.

Preference is given to compounds of the formula (I) in which a) m represents the number 0,
n represents the number 1 and
Y represents 2-chloro, 2-fluoro, 4-bromo, 2-methyl, 2-trifluoromethyl, 3-trifluoromethyl,
represents nitro, cyano, hydroxyl, carboxyl, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety, or b) m represents the number 0,
n represents the number 2 or 3 and
Y represents fluorine, chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety, or c) m represents the number 1,
X represents chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine, and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety,
n represents integers from 0 to 3 and
Y represents fluorine, chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety.

Particular preference is given to compounds of the formula (I) in which a) m represents the number 0,
n represents the number 1 and
Y represents 2-chloro, 2-fluoro, 4-bromo, 2-methyl, 2-trifluoromethyl, 3-trifluoromethyl,
represents nitro, cyano, hydroxyl, carboxyl, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl, or b) m represents the number 0,
n represents the number 2 or 3 and
Y represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl, or c) m represents the number 1,
X represents chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl, n represents integers from 0 to 3 and Y represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl.

The abovementioned definitions can be combined with one another as desired. Moreover, individual definitions may not apply.

Using 1,3-dimethyl-5-fluoropyrazole-4-carbonyl chloride and 2-(4-bromo-phenyl)-aniline as starting materials, the course of the process according to the invention can be illustrated by the formula scheme below.

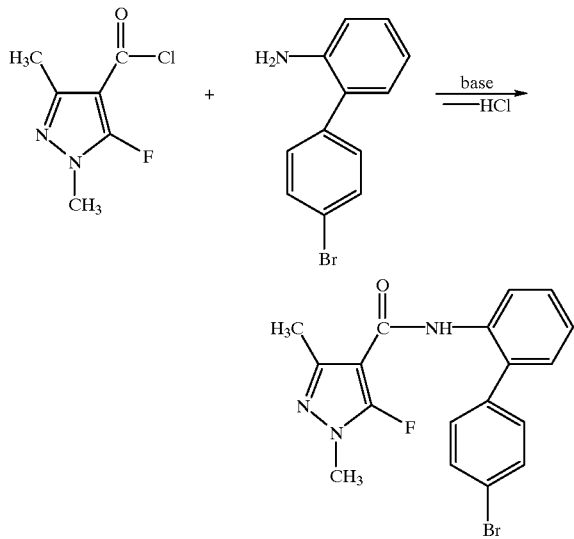

The formula (II) provides a general definition of the acyl halides required as starting, materials for carrying out the process according to the invention. In this formula, Hal preferably represents fluorine, chlorine or bromine.

The acyl halides of the formula (II) are known or can be prepared by known processes (cf. WO 93/11 117 and EP-A 0 776 889).

The formula (III) provides a general definition of the aniline derivatives required as reaction components for carrying out the process according to the invention. In this formula, X, Y, m and n each preferably have those meanings which have already been mentioned in connection with the description of the substances of the formula (I) according to the invention as being preferred for these radicals or these indices.

The aniline derivatives of the formula (III) are known or can be prepared by known methods (cf. EP-A 0 545 099 and EP-A 0 589 301).

Suitable acid binders for carrying out the process according to the invention are all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine N-methylpiperidine, N,N-dimethylaminopyridine, diazabicyclooctane (DABCO), diazabicyclononene (DBN) or diazabicycloundecene (DBU). However, it is also possible to carry out the process without an additional acid binder, or to use an excess of the amine component, so that it simultaneously acts as acid binder.

Suitable diluents for carrying out the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitrites, such as acetonitrile, propionitrile, n- or i-butyronitrile or benzonitrile; amides, such as N,N-dimethyl-formamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out the process according to the invention, the reaction temperatures can be varied within a relatively wide range. In general, the process is carried out at temperatures between 0° C. and 140° C., preferably between 10° C. and 120° C.

The process according to the invention is generally carried out under atmospheric pressure. However, it is also possible to operate in each case under elevated or reduced pressure.

When carrying out the process according to the invention. in general 1 mol or else an excess of the aniline derivative of the formula (III) and from 1 to 3 mol of acid binder are employed per mole of acyl halide of the formula (II). However, it is also possible to use other ratios of the reaction components. Work-up is carried out by customary methods. In general, the reaction mixture is admixed with water and the organic phase is separated off and, after drying, concentrated under reduced pressure. The residue that remains can, if appropriate, be freed of any impurities that may still be present, using customary methods. such as chromatography or recrystallization.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Altemaria brassicae;* and

Pseudocercosporella species, such as, for example, *Pseudocercosporella herpotrichoides.*

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling diseases in viticulture and in fruit and vegetable growing, such as, for example against Venturia, Botrytis, Sclerobinia, Rhizoctonia, Uncinula, Sphaerotheca, Podosphaera, Altemaria and Colletotriclum species. Rice diseases, such as Pyricularia and Pellicularia species are likewise controlled with good results.

The active compounds according to the invention are also suitable for increasing the yield of crops. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds or compositions according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia. such as *Escherichia coli,*

Pseudomonas, such as *Pseudomonas aeruginosa,* and

Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be employed in mixtures with known fungicides, bactericides, acaricides, nematicides or insecticides, to broaden, for example, the activity spectrum, or to prevent the development of resistance. In many cases, synergistic effects are obtained, i.e. the activity of the mixture is greater than the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazaili, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinoxyfen, sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl) ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl[(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-((6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin, Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demneton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimphos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazophos, isofenphos, isoxathion, ivermectin, nuclear polyhedrosis viruses, lambda-cyhalothrin, lufenuron, malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenophos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazarnate, triazophos, triazuron, trichlophenidine, trichlorfon, triflumuron, trimethacarb, vamidothion, vaniliprole, Verticillium lecanii,

YI 5302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropane carboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl] -4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimum rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in the protection of materials, or of the compositions, concentrates or quite generally formulations preparable therefrom, can be increased by, if appropriate, adding other antimicrobially active compounds, fungicides, bactericides, herbicides, insecticides or other active compounds for broadening the activity spectrum or obtaining particular effects, such as, for example, the additional protection against insects. These mixtures may have a broader activity spectrum than the compounds according to the invention.

The preparation and the use of the substances according to the invention is illustrated by the examples below.

PREPARATION EXAMPLES

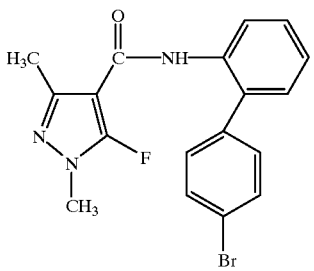

At room temperature, a solution of 2.5 g (0.01 mol) of 2-(4-bromo-phenyl)-aniline in 30 ml of toluene is admixed with 1.0 g (0.01 mol) of triethylamine. At room temperature, 1.8 g (0.01 mol) of 1,3-dimethyl-5-fluoro-pyrazole-4-carbonyl chloride are added with stirring to this mixture. After the addition has ended, the reaction mixture is stirred at room temperature for two hours and then poured into water. The mixture is extracted repeatedly with chloroform. The combined organic phases are dried over sodium sulphate, filtered and concentrated under reduced pressure. The residue that remains is stirred with diisopropyl ether. The resulting crystalline product is filtered off with suction and dried. This gives 1.6 g (41.2% of theory) of N-[2-(4-bromophenyl)]-1,3-dimethyl-5-fluoro-pyrazole-4-carboxanilide in the form of a solid of melting point 127° C.

The pyrazole-carboxanilides of the formula (I) listed in the table below are likewise prepared in the manner described above.

TABLE 1

| Example No. | | Physical constant |
|---|---|---|
| 2 | CH₃ (2,2'-dimethylbiphenyl) | m.p. 100° C. |
| 3 | Cl (2'-chloro-2-methylbiphenyl) | ¹H-NMR* δ = 2.34 (3H) 3.61 (3H) |
| 4 | CF₃ (2'-trifluoromethyl-2-methylbiphenyl) | m.p. 103° C. |
| 5 | F (2'-fluoro-2-methylbiphenyl) | m.p. 113° C. |
| 6 | CH₃ (substituted pyridyl-phenyl with CH₃ groups) | m.p. 127° C. |
| 7 | H₃C...CH₃ (trimethylbiphenyl) | m.p. 89° C. |

TABLE 1-continued (I)

| Example No. | [biphenyl substituent structure] | Physical constant |
|---|---|---|
| 8 | 2'-methyl-biphenyl with 3-Cl, 4-CH₃ | ¹H-NMR* δ = 2.38 (3H) 2.45 (3H) |
| 9 | 2'-methyl-biphenyl with 3-CF₃ | m.p. 116° C. |
| 10 | 2'-methyl-biphenyl with 2,3-(CH₃)₂ | m.p. 145° C. |
| 11 | 2-methyl-4-methyl-biphenyl | m.p. 151° C. |
| 12 | 4-methoxy-2-methyl-biphenyl with 4'-Cl | m.p. 154° C. |
| 13 | 4-methyl-2-methyl-biphenyl with 4'-Cl | m.p. 176° C. |
| 14 | 4-methoxy-2-methyl-biphenyl | m.p. 153° C. |
| 15 | 2-methyl-biphenyl with 4'-CN | m.p. 169° C. |
| 16 | 2,6-dimethyl-biphenyl | m.p. 144° C. |
| 17 | 2,6-dimethyl-biphenyl with 4'-Cl | m.p. 177° C. |
| 18 | 2-methyl-biphenyl with 4'-SCF₃ | m.p. 154° C. |
| 19 | 2-methyl-biphenyl with 3',4'-(CH₃)₂ | oil |
| 20 | 2-methyl-biphenyl with 3',4'-Cl₂ | m.p. 168° C. |
| 21 | 2-methyl-biphenyl with 3',5'-Cl₂ | m.p. 169° C. |

TABLE 1-continued

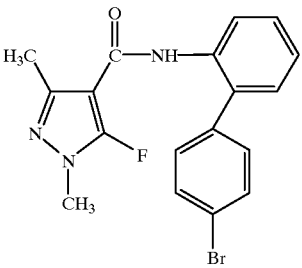

| Example No. | | Physical constant |
|---|---|---|
| 22 | 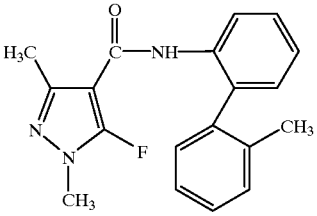 | m.p. 168° C. |
| 23 | | |
| 24 | | m.p. 172° C. |

*The ¹H-NMR spectra were recorded in deuterochloroform (CDCl₃) using tetramethylsilane (TMS) as internal standard. What is stated is the chemical shift as δ value in ppm.

USE EXAMPLES

Example A

| Podosphaera test (apple)/protective | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

Podosphaera test (apple)/protective

| Active compound | Application rate of active compound in g/ha | Efficacy in % |
|---|---|---|
| According to the invention: | | |
| (1) 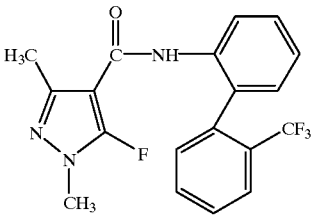 | 100 | 100 |
| (2) | 100 | 96 |
| (4) | 100 | 97 |
| (5) 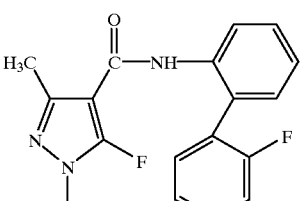 | 100 | 99 |

TABLE A-continued

Podosphaera test (apple)/protective

| Active compound | Application rate of active compound in g/ha | Efficacy in % |
|---|---|---|
| (8) 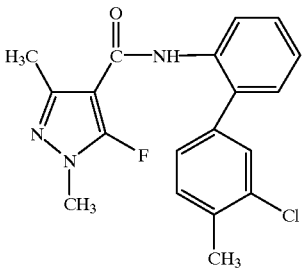 | 100 | 98 |
| (9) 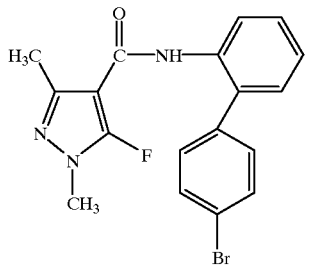 | 100 | 100 |

Example B

Sphaerotheca test (cucumber)/protective

| Solvent: | 47 parts by weight of acetone |
|---|---|
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed at about 23° C. and a relative atmospheric humidity of about 70% in a greenhouse.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

Sphaerotheca test (cucumber)/protective

| Active compound | Application rate of active compound in g/ha | Efficacy in % |
|---|---|---|
| According to the invention: | | |
| (1) 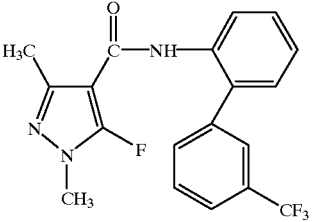 | 100 | 95 |
| (9) 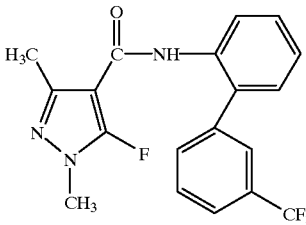 | 100 | 94 |

Example C

Venturia test (apple)/protective

| Solvent: | 47 parts by weight of acetone |
|---|---|
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at 20° C. and 100% relative atmospheric humidity for 1 day.

The plants are then placed in a greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE C

Venturia test (apple)/protective

| Active compound | Application rate of active compound in g/ha | Efficacy in % |
|---|---|---|
| According to the invention: | | |
| (1) [H₃C-pyrazole(CH₃,F)-C(O)-NH-phenyl-phenyl-Br structure] | 100 | 100 |
| (8) [H₃C-pyrazole(CH₃,F)-C(O)-NH-phenyl-phenyl(Cl,CH₂) structure] | 100 | 100 |
| (9) [H₃C-pyrazole(CH₃,F)-C(O)-NH-phenyl-phenyl-CF₃ structure] | 100 | 97 |

Example D
Erysiphe test (barley)/protective

| Solvent: | 48.8 parts by weight of N,N-dimethylformamide |
|---|---|
| Emulsifier: | 1.2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young cereal plants are sprayed with the preparation of active compound at the stated application rate. 1 day after the treatment, the plants are inoculated with spores of *Erysiphe graminis* f. sp. *hordei*. The plants are then placed in a greenhouse at 70% relative atmospheric humidity and a temperature of 18° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

Erysiphe test (barley)/protective

| Active compound | Application rate of active compound in g/ha | Efficacy in % |
|---|---|---|
| (2) [pyrazole(CH₃,CH₃,F)-CO-NH-phenyl-phenyl-CH₃ structure] | 750 | 90 |
| (1) [H₃C-pyrazole(CH₃,F)-C(O)-NH-phenyl-phenyl-Br structure] | 750 | 100 |
| (16) [H₃C-pyrazole(CH₃,F)-C(O)-NH-phenyl(CH₃)-phenyl structure] | 750 | 94 |
| (17) [H₃C-pyrazole(CH₃,F)-C(O)-NH-phenyl(CH₃)-phenyl-Cl structure] | 750 | 100 |

Example E

Pyrenophora teres test (barley)/protective

| Solvent: | 25 parts by weight of N,N-dimethylacetamide |
|---|---|
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of about 20° C. and a relative atmospheric humidity of about 80%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE E

Pyrenophora teres test (barley)/protective

| Active compound | Application rate of active compound in g/ha | Efficacy in % |
|---|---|---|
| (1) 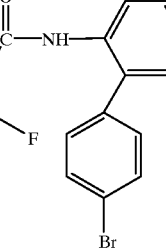 | 250 | 100 |
| (8) 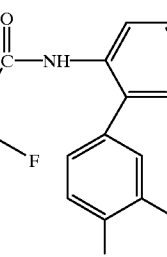 | 250 | 100 |
| (9) 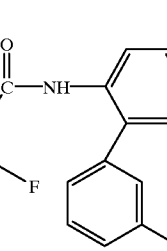 | 250 | 100 |
| (17) | 250 | 100 |

TABLE E-continued

Pyrenophora teres test (barley)/protective

| Active compound | Application rate of active compound in g/ha | Efficacy in % |
|---|---|---|
| 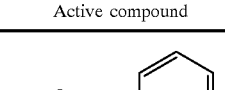 | | |

What is claimed is:

1. A pyrazole-carboxanilide of the formula

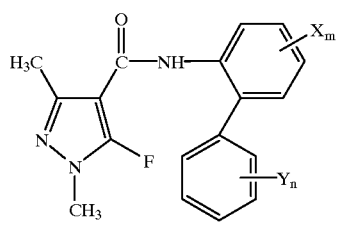

(I)

wherein a) m represents the number 0,
   n represents the number 1 and
   Y represents 2-chloro, 2-fluoro, 4-bromo, 2-methyl, 2-trifluoromethyl, 3-trifluoromethyl,
   or
   represents nitro, cyano, hydroxyl, carboxyl, halogenoalkoxy having 1 to 6 carbon atoms and 1 to 5 halogen atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety,
   or
b) m represents the number 0,
   n represents the number 2 or 3 and
   Y represents halogen, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety, or c) m represents the number 1, X represents chlorine, bromine, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety, n represents integers from 0 to 3 and Y represents halogen, nitro, cyano, hydroxyl, carboxyl, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety.

2. A pyrazole-carboxanilide of the formula (I) according to claim 1, wherein a) m represents the number 0, n represents the number 1 and Y represents 2-chloro, 2-fluoro, 4-bromo, 2-methyl, 2-trifluoromethyl, 3-trifluoromethyl, or represents nitro, cyano, hydroxyl, carboxyl, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety, or b) m represents the number 0, n represents the number 2 or 3 and Y represents fluorine, chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety, or c) m represents the number 1, X represents chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms or 1 to 5 fluorine, chlorine, and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety, n represents integers from 0 to 3 and Y represents fluorine, chlorine, bromine, nitro, cyano, hydroxyl, carboxyl, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carboalkoxy having 1 to 4 carbon atoms in the alkoxy moiety or represents alkoximinoalkyl having 1 to 4 carbon atoms in the alkoxy moiety and 1 to 4 carbon atoms in the alkyl moiety.

3. A pyrazole-carboxanilide according to claim 1, having the formula

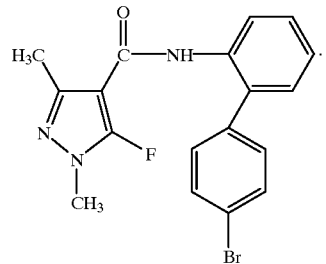

4. A pyrazole-carboxanilide according to claim 1, having the formula

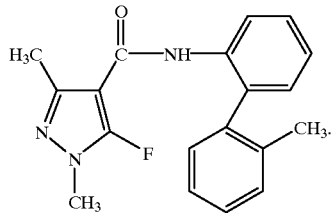

5. A pyrazole-carboxanilide according to claim 1, having the formula

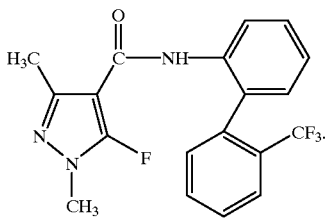

6. A process for preparing pyrazole-carboxanilides of the formula (I) according to claim 1, comprising the step of reacting acyl halides of the formula

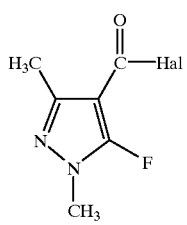

(II)

wherein
Hal represents halogen,
with aniline derivatives of the formula

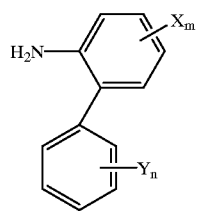

(III)

wherein
X, Y, m and n are each as defined in claim 1.

7. A composition for controlling undesirable microorganisms, comprising one or more pyrazole-carboxanilide of the formula (I) according to claim 1, in addition to extenders and/or surfactants.

8. A method for controlling undesirable microorganisms, comprising the step of applying one or more pyrazole-carboxanilides of the formula (I) according to claim 2 to the microorganisms and/or their habitat.

9. A method for controlling undesirable microorganisms, comprising the step of applying one or more pyrazole-carboxanilides of the formula (I) according to claim 1 to the microorganisms and/or their habitat.

10. A process for preparing compositions for controlling undesirable microorganisms, comprising the step of mixing one or more pyrazole-carboxanilides of the formula (I) according to claim 1 with extenders and/or surfactants.

11. A process according to claim 6, wherein the step of reacting acyl halides with aniline derivatives occurs in the presence of an ingredient selected from the group consisting of acid binders, diluents and mixtures thereof.

12. A pyrazole-carboxanilide of the formula (I) according to claim 1, wherein m represents the number 0, n represents the number 1 and Y represents 2-chloro, 2-fluoro, 4-bromo, 2-methyl, 2-trifluoromethyl, 3-trifluoromethyl, or represents nitro, cyano, hydroxyl, carboxyl, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl.

13. A pyrazole-carboxanilide of the formula (I) according to claim 1, wherein m represents the number 0, n represents the number 2 or 3 and Y represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl.

14. A pyrazole-carboxanilide of the formula (I) according to claim 1, wherein m represents the number 1, X represents chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl, n represents integers from 0 to 3 and Y represents fluorine, chlorine, bromine, nitro, cyano, hydroxyl, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, methylthio, difluoromethoxy, trifluoromethoxy, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl.

* * * * *